United States Patent [19]

Stanley

[11] Patent Number: 4,863,422
[45] Date of Patent: Sep. 5, 1989

[54] SWAB APPLICATOR FOR GENERATION OF HEATED MEDICAMENT

[76] Inventor: Sharon Stanley, 438 Wilson Mill Rd., Atlanta, Ga. 30331

[21] Appl. No.: 206,749

[22] Filed: Jun. 15, 1988

Related U.S. Application Data

[63] Continuation-in-part of Ser. No. 56,695, Jun. 2, 1987, Pat. No. 4,776,836.

[51] Int. Cl.⁴ ............................................. A61M 35/00
[52] U.S. Cl. ......................................... 604/3; 604/291
[58] Field of Search ........................................ 604/1–3, 604/113, 291; 401/1, 132

[56] References Cited

U.S. PATENT DOCUMENTS

| | | | |
|---|---|---|---|
| 2,907,782 | 10/1959 | Cohen | 604/113 |
| 3,757,782 | 9/1973 | Aiken | 604/3 |
| 4,776,836 | 10/1988 | Stanley | 604/3 |

Primary Examiner—Dalton L. Truluck
Attorney, Agent, or Firm—Jerome J. Norris

[57] ABSTRACT

A double ended compressible tubular swab applicator comprising a length of tubular material containing a charge of a treating liquid in an innermost lumen and a heat generating material having microencapsulated water spheres embedded in an outermost lumen, for delivery of heated treating liquid upon compression of the microcapsules and rupturing of sealing members.

6 Claims, 1 Drawing Sheet

SWAB APPLICATOR FOR GENERATION OF HEATED MEDICAMENT

BACKGROUND OF THE INVENTION

This application is a continuation in-part of U.S. Ser. No. 056,695, filed June 2, 1987, now U.S. Pat. No. 4,776,836 issued Oct. 11, 1988, and pertains to new and useful improvements in swab applicators for delivering heated medicaments.

Heated or body temperature medicaments such as antiseptics and the like are in high demand for use in hospitals, physicians' and surgeons' offices and clinics and homes. However, in all of these usages, an external source of heating means, separate and apart from the applicator, are generally required in order to heat the medicament or bring it up to body temperature or higher.

In particular, when the medicament, antiseptic or lubricant needs to be applied to a part of the body from an applicator it is necessary to first heat the medicament in a different vessel than the applicator by a source of heat which is not part of the applicator, and thereby run the risk of contaminating the medicament.

FIELD OF THE INVENTION

When the applicator used for supplying the medicament is a tubular double ended swab applicator, which is capable of saturating a swab end upon pressurization of the tubular member to release a stored charge of confined medicament, there is no means for directly applying the medicament from the tubular member to the swab end as a heated solution for direct application to a part of the body.

SUMMARY OF THE INVENTION

The present invention provides a double ended tubular swab applicator which can directly supply heat treating liquids such as medicaments, antiseptics and lubricants to saturate a swab end, for direct application to a particular region of a patient's body, without the need of dipping the swab into a bottle of the medicament, which has been heated by external sources which form no part of the applicator.

This is accomplished by utilizing a double ended swab applicator in which a charge of the medicament or solution is confined and provisionally sealed by a frangible material within an innermost flexible plastic tube, and wherein the tube ends are embedded within an applicator material, such as a quantity of wound cotton. The innermost plastic tube containing the medicament charge is surrounded by a heat generating or exothermic producing matrix in which rupturable microencapsulated shells of water are embedded.

When an outer wall in which the heat generating material containing the microencapsulated water is pressurized by force from the fingers and thumb, the microcapsules or shells are ruptured to release water into the heat generating material which surrounds the medicament charged innermost tube. After a short period, and when the heated medicament is ready for application to a body part, a frangible seal situated between the ends of the tubular member is broken by bending the flexible tubular member in order to allow the confined heated medicament to flow freely and saturate a swab end.

Therefore, it is an object of the present invention to provide a double ended tubular swab applicator which allows a confined heated charge of medicament to be applied to a body member, without the need for supplying heating means from a source exterior to the applicator and without the need to dip swab portions of the applicator into a separate vial of heated medicament.

A further object of the invention is to provide a double ended tubular swab applicator having integral means for heating a charge of confined medicament, as an integral part of the application structure.

A yet further object of the invention is to provide a double ended tubular swab applicator having microencapsulated water embedded in a matrix of a heat generating material in order to generate heat to a confined medicament charge, for subsequent application via a saturated swab to a portion of a patient's body.

These and other objects of the invention will become apparent from the invention description hereinafter set forth.

DETAILED DESCRIPTION OF THE INVENTION

Figure 1:
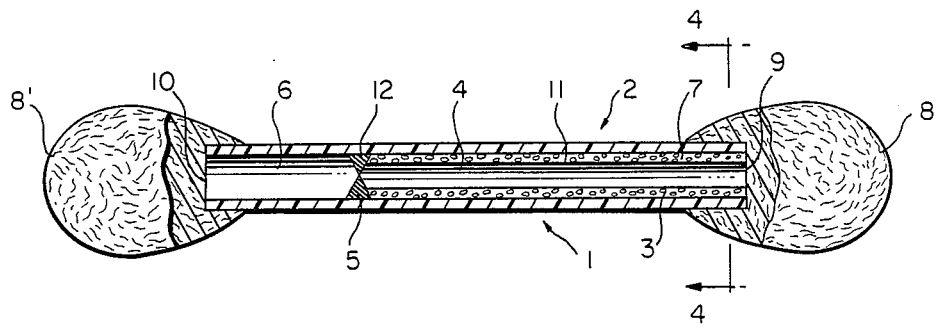
FIG. 1 is a view in perspective of a tubular fluid pressurizable double swab applicator before use, in longitudinal section, and in a plane which includes the axis of the handle member.

FIG. 1 illustrates a tubular applicator generally designated by the numeral 1, comprising an elongated tubular handle rod 2, which has an outside diameter of from about 3/16 of an inch to about ⅜ of an inch or larger. The handle rod is extruded and is made of a compressible and flexible synthetic plastic that is inert to the heat generating material 3 and the medicament charge 4. The medicament charge fills the innermost lumen or tubular space between an internal frangible seal 5, which is fused in place between sub-compartment 6 at one end of the tubular applicator and the double lumen compartment which contains the outer lumen heat generating material in which microencapsulated water 7 is embedded and the inner lumen which contains the medicament charge.

The heat generating material which can be used is comprised of the following materials:

| | |
|---|---|
| Iron, 60 mesh | 17 ounces |
| Manganese hydroxide | 1 ounce |
| (manganese hydrate precipitated) | |
| Graphitic carbon | 30 grains |
| Ferric chloride | 30 grains |
| Ferrous sulfate | 30 grains |
| Manganese chloride | 30 grains |
| Manganese sulfate | 30 grains |

Before water, which is encapsulated in vinylidene chloride, is placed in the mixture, some form of silica which has the property of retaining moisture, such as kieselguhr, silica gel or sodium silicate should be added to the heat generating material. These silica materials provide a protective effect in the event the mixture is unduly exposed to a humid atmosphere before, during or after the time it is placed in the outer lumen to the tubular applicator. Any moisture entering the mixture from this atmosphere is taken up by these silica absorbing substances and later given off into the surrounding atmosphere when and if drier conditions prevail, thus preventing unintentional reaction and preserving the life of the mixture. Moreover, when water is allowed to enter the heat generating composition by squeezing the applicator at the appropriate areas to rupture or break the microcapsules, the water is more thoroughly diffused because of the retarding or restricting effect of these silica compounds.

It has been found that kieselguhr, silica gel or sodium silicate can be added to the above heat generating mixture to provide the moisture retaining effect in a quantity of about 30 grains.

Figure 2:
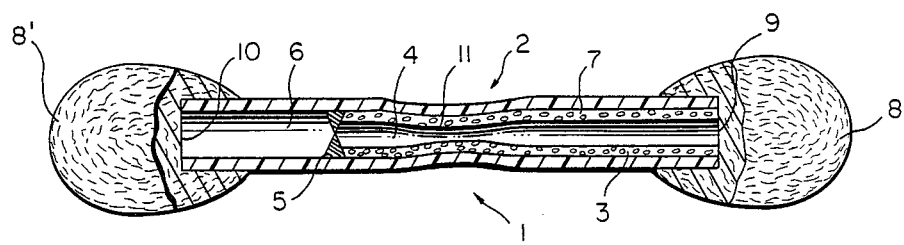
FIG. 2 is a view in longitudinal section of the tubular fluid pressurizable double swab applicator illustrating the action upon the outer chamber or lumen containing the heat generating material in which microencapsulated water spheres are embedded.
Figure 3:
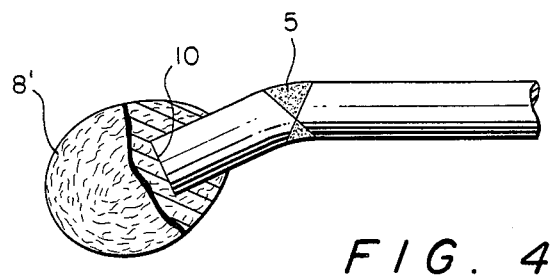
FIG. 3 is a view illustrating action upon the frangible sealing partition which internally subdivides the tubular applicator upon bending the applicator in the vicinity of the partition, in order to create flowability and saturate an end swab with a heated medicament.

When it is desired to heat the medicament charge which has been injected into the inner or interior lumen of the applicator, the vinylidene chloride microencapsulated spheres of water are broken by the exertion of force arising from kneading the outside diameter of the appropriate area of the applicator to produce the action as shown in FIG. 2. Heat is promptly generated through the circumferential plastic wall 11 that separates the inner and outer lumens. After a period of up to about one 1 minute or longer, and immediately before it is desired to saturate swab member 8 with the heated medicament for application to a portion of the body, the applicator is bent at the area around the internal frangible seal 5, as shown in FIG. 3 in order to break the partition, which is preferably in the form of two inverted pyramidal structures joined at their apices or highest points. The base portions of the pyramid which permanently seal the heat generating material and encapsulated water in the outer lumen is made of a non-frangible material; however, the upper portions of the pyramids which form a non-permanent seal for the medicament in the inner lumen is frangible, and is made so by well-known means such as chemical etching or physical scoring.

After the frangible seal is broken, the memory effect of the plastic tubular member restores it to a straightened position. Thereafter, renewed squeezing is affected along the entire length of the tubular applicator in order to rupture end membrane element 10 from the created hydraulic pressure. Element 10 is provisionally sealed across the tube end, either adhesively or by a fused connection; however, it is necessary that end membrane element 10 is easily rupturable by hydraulic pressure caused by the heated medicament charge upon squeezing, in order to saturate cotton swab member 8' prior to applying the heated medicament to a part of the body.

It is also essential that end membrane element 9 be integral to the tubular end and non rupturable by the hydraulic pressure of the medicament charge, as this arrangement allows swab member 8 to remain dry and free for use to dry the part of the body which is cleansed by the heated medicament from the saturated swab member.

As can be seen from the figures, end element 10 is sufficiently positioned in the interior of the swab member i.e., by ensuring that the swab is wound about or otherwise secured to the tubular end, so that the compression from squeezing, after breaking the frangible seal, is adequate to completely saturate the swab when the end element is ruptured.

Figure 4:
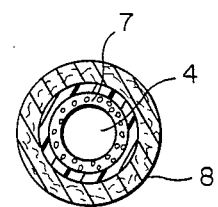
FIG. 4 is a view in transverse section along lines 4—4 of FIG. 1.

FIG. 4 is a view in transverse section along line 4—4 of FIG. 1, illustrating the hollow interior or inner lumen in which the medicament charge is confined and the surrounding or outer lumen in which the heat generating material containing embedded microcapsules of water is confined. Circumferential wall 11 and non rupturable seal 12 are plastics of sufficient thickness to prevent any of the heat generating materials from entering into the lumen or chamber containing the medicament charge.

While the preferred material for encapsulating water is vinylidene chloride, which is known as Saran*, Nylon* will also suffice in the context of the invention as a microencapsulant. The chief criterion is that the encapsulant wall must stop water and yet be rupturable upon exertion of pressure to release the water.

* Registered.

Also, it should be noted that any heat generating material that does not react with the plastic wall that divides it from the medicament charge will work in the context of the invention. For example, it has been found that a mixture of the following materials will also suffice:

|  | By weight |
| --- | --- |
| Crushed cast iron | 95 parts |
| Crushed carbon steel | 5 parts |
| Epsom salt | 0.5 parts |
| Sodium chloride | 0.5 parts |
| Ammonium chloride | 0.25 parts |

It will be obvious to those skilled in the art that many changes can be made in the double ended swab applicator for generation of a heated medicament without departing from the spirit of the invention, and that the description and examples are illustrative only, and not intended to limit the invention scope, which is indicated by the appended claims.

What is claimed is:

1. A double ended swab applicator adapted to provide heat to a confined charge of a treating liquid upon squeezing, comprising: a length of compressible tubular material having the ends embedded in a swab material and having an inner lumen and an outer lumen concentric therewith extending within said tubular member; said length of tubular material having an internal seal of inverted pyramidal structures subdividing the innermost and outermost lumen on one side and a hollow chamber at another side; wherein said innermost lumen contains a charge of treating liquid and said outermost lumen contains a heat generating material having rupturable microencapsulated water spheres embedded therein; and wherein said inverted pyramidal structures have base portions which are non-frangible to seal the outermost lumen and upper portions which are frangible to seal the innermost lumen.

2. The double ended compressible tubular swab of claim 1, wherein said hollow chamber is end-stopped by a rupturable membrane element, and wherein said innermost and outermost lumens are end stopped by a permanent non-rupturable seal.

3. The double ended compressible tubular swab of claim 2, wherein the heat generating material is composed of:

| | |
|---|---|
| Iron, 60 mesh | 17 ounces |
| Manganese hydroxide | 1 ounce |
| Graphite carbon | 30 grains |
| Ferric chloride | 30 grains |
| Ferrous sulfate | 30 grains |
| Manganese chloride | 30 grains |
| Manganese sulfate | 30 grains |

4. The double ended compressible tubular swab of claim 3, further containing about 30 grains of a moisture silica selected from the group consisting of kieselguhr, silica gel or sodium silicate.

5. The double ended compressible tubular swab of claim 4, wherein the microencapsulating material is vinylidene chloride.

6. The double ended compressible tubular swab of claim 2 wherein the heat generating material is composed by weight of:

| | |
|---|---|
| Crushed cast iron | 95 parts |
| Crushed carbon steel | 5 parts |
| Epsom salt | 0.5 parts |
| Sodium chloride | 0.5 parts |
| Ammonium chloride | 0.25 parts |

* * * * *